United States Patent [19]

Aliev et al.

[11] 4,237,323

[45] Dec. 2, 1980

[54] METHOD FOR PREPARING α-NAPHTHOL

[76] Inventors: Sakhib M. O. Aliev, ulitsa Barinova, 12, blok 4, kv. 31; Vagab S. Aliev, ulitsa Nizami, 66, blok 5, kv. 40; Novruz I. O. Guseinov, poselok N. Akhmedly 1730 proezd, 13, kv. 96; Vagif A. O. Nagiev, ulitsa Neftepererabotchikov, 170, kv. 181; Nuri T. O. Sultanov, ulitsa Pushkina, 12/14, kv. 21, all of Baku, U.S.S.R.

[21] Appl. No.: 46,647

[22] Filed: Jun. 8, 1979

[51] Int. Cl.$^3$ ............................................. C07C 37/04
[52] U.S. Cl. ................................................... 568/738
[58] Field of Search .............................. 568/738, 736

[56] References Cited

U.S. PATENT DOCUMENTS

| | | | |
|---|---|---|---|
| 1,949,243 | 2/1934 | Cotton | 568/738 |
| 1,962,137 | 6/1934 | Cotton | 568/738 |
| 2,025,197 | 12/1935 | Cotton | 568/738 |

OTHER PUBLICATIONS

Erros et al., "Chemistry and Processes for the Production of Aromatic Compounds", Khimia Publishers, Leningrad, 1971, p. 73.

*Primary Examiner*—Werren B. Lone
*Attorney, Agent, or Firm*—Lackenbach, Lilling & Siegel

[57] ABSTRACT

A method for preparing α-naphthol according to the present invention comprises sulphonation of naphthalene with an equimolar amount of a concentrated sulphuric acid at a temperature ranging from 30° to 85° C. for a period of from 60 to 120 minutes in the presence of acetic anhydride taken in an amount of from 0.5 to 1.5 mole per mole of naphthalene. The resulting naphthalene-α-sulphonic acid is fused with an alkali taken in an amount of 3–4 moles per mole of naphthalene-α-sulphonic acid at a temperature ranging from 180° to 285° C. for a period of from 10 to 30 minutes. The resulting melt consisting of the alkali metal α-naphtholate and the alkali metal sulphite is mixed with a polar solvent; the resulting mixture is acidified with a mineral acid taken in an amount equimolar relative to the alkali metal α-naphtholate, whereafter α-naphthol is separated from the resulting suspension. The method according to the present invention makes it possible to increase the yield of α-naphthol up to 98% of the theoretical amount and produce α-naththol with a purity of up to 99.5%.

8 Claims, No Drawings

METHOD FOR PREPARING α-NAPHTHOL

FIELD OF THE INVENTION

The present invention relates to methods for preparing α-naphthol which is employed in the production of an insecticide for cutworm, i.e. α-naphthyl ether of N-methylcarbamine acid, as well as in the production of azodyes. Furthermore, α-naphthol is an efficient antioxidant which is added to mineral and vegetable oils.

BACKGROUND OF THE INVENTION

Known in the art is a method for preparing α-naphthol by sulphonation of naphthalene with a 96–98% sulphuric acid taken in a 1.5–2-fold excess at a temperature ranging from 20° to 75° C. Then the resulting sulpho mass consisting of naphthalenesulphonic acids, unreacted sulphuric acid, water and impurities (such as sulphones, disulphonic acids) is diluted with water in a 3.5-fold excess. To separate the unreacted sulphuric acid, the aqueous solution of the sulpho mass is treated with lime and the precipitated $CaSO_4$ is separated therefrom. Thereafter, the resulting calcium salt of naphthalenesulphonic acid in the form of an aqueous solution is converted, by means of $Na_2CO_3$, to a sodium salt of naphthalenesulphonic acid. Afterwards, the thus-prepared aqueous solution of sodium salt of naphthalenesulphonic acid is treated with hydrogen chloride to neutralize the excess soda. The resulting mixture is evaporated and dried. As a result, after drying a product is obtained having the following composition, percent by weight:

| | |
|---|---|
| sodium salt of naphthalene-β-sulphonic acid | 10.2 |
| sodium salt of naphthalene-α-sulphonic acid | 77.5 |
| disulphonate | 5.7 |
| sodium sulphate | 2.9 |
| water | 3.7 |

As is clearly seen from the data, the resulting sodium salt of naphthalene-α-sulphonic acid is diluted with β-isomer and disulphonate.

A mixture of naphtholates and an alkali metal sulphite contaminated with an alkali metal sulphate and resinous compounds is obtained by melt fusion of sodium salts of naphthalenesulphonic acids with potassium hydroxide or sodium hydroxide at a temperature of 290° C. for 8 hours.

Said mixture of the fusion products is diluted with water taken in a great excess and acidified with sulphuric or hydrochloric acid at a temperature ranging from 70° to 95° C. Mineral acids are also taken in an excess of 2–4 moles per mole of the naphtholate.

Then the resulting mixture in the form of an aqueous solution consisting of naphthols, and alkali metal sulphate or chloride, the unreacted sulphite, resinous compounds and other impurities is cooled to room temperature. In doing so, a mixture of 89% by weight of α-naphthol and 11% by weight of β-naphthol is precipitated from the solution.

The yield of α-naphthol is 79 mol.% as calculated for the starting naphthalene. The resulting α-naphthol contains more than 10% by weight of β-naphthol which makes it unsuitable in the production of α-naphthyl ether of N-methylcarbamine acid or in the synthesis of α-naphthylamine containing no strongly carcinogenic β-naphthylamine.

Therefore, this prior art (prototype) method has the following disadvantages:
low yield and purity of α-naphthol,
a high rate of consumption of the reactants,
the formation of hardly-utilized wastes: gypsum, acidic waters, disulphonates and resinous products.

In addition, a disadvantage of the prior art method resides in the complicated process equipment employed.

Due to the above-mentioned disadvantages the prior art method discussed hereinabove is not suitable for the preparation of a high-purity α-naphthol.

SUMMARY OF THE INVENTION

It is an object of the present invention to provide a method for preparing α-naphthol which would make it possible to increase the yield of α-naphthol simultaneously with increasing its purity.

This object is accomplished by a method for preparing α-naphthol which involves sulphonation of naphthalene with concentrated sulphuric acid at a temperature ranging from 30° to 85° C.; in accordance with the present invention, taken for sulphonation is an equimolar amount of sulphuric acid and the process is conducted for 60 to 120 minutes in the presence of acetic anhydride taken in an amount of from 0.5 to 1.5 mole per mole of naphthalene, whereafter the thus-prepared naphthalene-α-sulphonic acid is fused, at a temperature ranging from 180° to 285° C. for 10–30 minutes, with an alkali taken in amount of 3–4 moles per one mole of naphthalene-α-sulphonic acid. The resulting melt consisting of an alkali metal α-naphtholate and an alkali metal sulphite is mixed with a polar solvent, the resulting mixture is acidified with a mineral acid taken in the equivalent amount relative to the amount of the alkali metal α-naphtholate, whereafter α-naphthol is recovered from the resulting suspension.

In order to minimize the corrosion-activity of the process medium and to produce carbonates of alkali metals (such as potash), carbonic acid is used for the melt acidification.

DETAILED DESCRIPTION OF THE INVENTION

The method according to the present invention is effected in the following manner.

Sulphonation of naphthalene is conducted using an equimolar amount of a concentrated sulphuric acid in the presence of acetic anhydride taken in the molar ratio to naphthalene equal to 0.5–1.5:1 at a temperature within the range of from 30° to 85° C. for a period of from 60 to 120 minutes.

The reaction products are naphthalene-α-sulphonic acid and acetic acid while impurities (naphthalene, disulphonic acids, sulphones and resinous products) are substantially absent. The content of naphthalene-β-sulphonic acid in the reaction mixture does not exceed 1% by weight. At the equimolar ratio between naphthalene, sulphuric acid and acetic anhydride there is attained a substantially total conversion of the reaction components with a maximum yield of naphthalene-α-sulphonic acid and acetic acid.

Sulphonation of naphthalene by the method according to the present invention from the very beginning and till completion of the reaction occurs in a homogeneous phase and can be performed in sulphators of periodic action and in flow-type reactors. Acetic acid formed during the sulphonation process is distilled off to give naphthalene-α-sulphonic acid with a purity of 98–99.5%. The resulting naphthalene-α-sulphonic acid is further fed to fusion with 3–4 moles of an alkali-metal hydroxide, preferably potassium hydroxide, at a temperature of from 180° to 285° C. for 10–30 minutes in a periodic-action or flow-type reactor. The fusion process within said temperature range also occurs in a homogeneous phase.

On completion of fusion the resulting melt consisting of the alkali metal α-phenolate, the alkali metal sulphite, impurities (alkali metal hydroxides and the alkali metal β-phenolate) is diluted with a polar solvent such as water, mono or di-hydric alcohol. The weight ratio between the melt and polar solvent is 1:1–3 respectively.

In the case of dilution of the melt with water, an aqueous solution of the alkali metal α-naphtholate and the alkali metal sulphite is formed. The resulting solution is mixed with a mineral acid taken in the equivalent amount relative to the alkali metal α-naphtholate. The mixture is cooled to a temperature of 10° to 25° C.; the resulting α-naphthol is precipitated, while mineral salts of alkali metals remain in the form of an aqueous solution. From the thus-formed suspension the precipitated α-naphthol is recovered by conventional means such as filtration, centrifugation or decantation. To remove impurities, (mineral salts of alkali metals dissolved in water), the recovered α-naphthol is repeatedly washed with a 2–3-fold weight excess of water.

The yield of crystalline α-naphthol of the 99.5% purity is 0.7–0.8 mole per mole of the naphthalene taken for the reaction. The content of β-naphthol in the resulting α-naphthol does not exceed 0.5% by weight. Other impurities are substantially lacking. The filtrate containing water, mineral salts of alkali metals and the non-precipitated α-naphthol and β-naphthol is treated with an organic solvent such as carbon tetrachloride (volume ratio between the filtrate and carbon tetrachloride is 1:0.25). After settlement, the organic layer containing naphthols is separated from the aqueous layer containing the above-mentioned salts. An additional 0.15–0.27 mole of α-naphthol with a purity of 95–98% is prepared by distilling-off the organic solvent. The content of β-naphthol in this additionally produced α-naphthol is 2–5% by weight. Other impurities are absent.

The total yield of α-naphthol is 0.95–0.98 mole (95–98% of the theoretical value) per mole of the employed naphthalene.

A mixture of mineral salts containing an alkali metal, preferably potassium, as the cation is produced from the aqueous layer by distilling-off water.

This mixture, after appropriate treatment is used in mineral fertilizer compositions.

The distilled water is recycled to the stage of dissolution of the product of the fusion of naphthalene-α-sulphonic acid and an the alkali (fusion melt).

In the case of dilution of the product of said alkali fusion of naphthalene-α-sulphonic acid with an alcohol, preferably ethanol, the alkali metal α-phenolate contained in the melt is dissolved in the alcohol, while the alkali metal sulphite is precipitated. The pure alkali metal sulphite is recovered from the resulting suspension by filtration or centrifugation. The solution of the alkali metal α-naphtholate in the alcohol is acidified with the equivalent amount, relative to the alkali α-naphtholate amount, of a mineral acid preferably carbonic acid at a temperature ranging from 20° to 60° C. The precipitated mineral salt of the alkali acid such as potassium carbonate is recovered in its pure form by means of filtration or centrifugation, while the resulting solution of α-naphthol in the alcohol is subjected to distillation. The resulting alcohol is repeatedly used for dilution of the products of said alkali fusion of naphthalene-α-sulphonic acid. The thus-prepared α-naphthol with a purity of 98–99% is subjected to vacuum close fractionation under a residual pressure of from 20 to 40 mm Hg to recover 0.75–0.85 mole of α-naphthol per mole of naphthalene employed for the reaction. The α-naphthol resulting from the fractionation has a purity of 99.5%. The residue after fractionation is subjected to vacuum distillation under a residual pressure of from 20 to 40 mm Hg to give 0.14–0.23 mole of α-naphthol per one mole of the starting naphthalene with the purity of 95–98%.

The total yield of α-naphthol is 0.96–0.98 mole per mole of the employed naphthalene which corresponds to 96–98% of the theoretical value.

In all cases, the acetic acid resulting from the sulphonation stage meets the requirements imposed on glacial acetic acid.

Therefore, the advantages of the method according to the present invention reside in an increased yield and better purity of α-naphthol, performing all the process stages in a homogeneous phase using a simplified technology, reduced consumption of sulphuric acid and alkali, absence of hardly-utilized by-products, wastes and contaminated waste waters.

An important advantage of the method according to the present invention resides in a separate production of the alkali metal sulphite and the alkali metal carbonate which ensures their efficient use in the production of cellulose and alkali metal cyanate and, consequently, improves technical and economic parameters of the process as a whole.

For a better understanding of the present invention, some specific Examples are given hereinbelow by way of illustration.

EXAMPLE 1

128 g (1 mole) of naphthalene are dissolved in 102 g (1 mole) of acetic anhydride in an apparatus with a stirrer and a means for the supply of sulphuric acid, a dephlegmator, cooler and vacuum-receiver. Then 98 g (1 mole) of a 100% sulphuric acid are added to the solution of naphthalene in acetic anhydride for 60 minutes at a temperature of 60° C. The removal of the forming acetic acid is effected under vacuum under a residual pressure of 1 to 10 mm Hg. After discontinuation of distillation of acetic acid, i.e. on completion of the reaction of naphthalene sulphonation, there are obtained 208 g (1 mole) of naphthalene-α-sulphonic acid and 118 g (2 moles) of glacial acetic acid. The resulting naphthalene-α-sulphonic acid is poured to 224 g (4 moles) of a preliminary prepared melt of potassium hydroxide having a temperature of 180° C. under vigorous stirring. Then the melt temperature is raised to 285° C. for 5 minutes and the melt is maintained at this temperature for 5 minutes to complete the fusion process. On expiration of 10 minutes, the melt is cooled to a temperature of 80° C., diluted with 200 g of water and the resulting aqueous solution containing potassium α-naphtholate and potassium sulphite is supplied into a mixer provided with a cooling jacket, whereinto a solution of 98 g (1 mole) of sulphuric acid in 400 g of water has been preliminarily charged. Then the resulting mixture is cooled to a temperature of 10° C. and the precipitated α-naphthol is separated from the aqueous solution of the mixture of potassium sulphite, potassium sulphate and non-precipitated α-naphthol and β-naphthol by filtration. The yield of α-naphthol with a purity of 99.5% is 115 g (0.8 mole) as calculated for the employed naphthalene which corresponds to 80% of the theoretical value. The filtrate is treated with an equal volume of carbon tetrachloride and, after separation of the aqueous layer and distilling-off carbon tetrachloride, there are obtained 25 g (0.17 mole) of α-naphthol with a purity of 95%. The total yield of α-naphthol is 97% of the theoretical as calculated for the employed naphthalene.

The aqueous layer is distilled-off to obtain a mixture of potassium sulphate and potassium sulphite. The distilled water is recycled to the stage of acidification of the products of the alkali fusion of naphthalene-α-sulphonic acid.

EXAMPLE 2

128 g (1 mole) of naphthalene are dissolved in 153 g (1.5 mole) of acetic anhydride. The resulting solution is added, under stirring, with 98 g (1 mole) of a 100% sulphuric acid for 95 minutes while gradually raising the temperature from 30° to 45° C. Further sulphonation of naphthalene is conducted at a temperature of 45° C. for an additional 45 minutes following the procedure described in the foregoing Example 1 to give 208 g of naphthalene-α-sulphonic acid, 145 g of glacial acetic acid and 25.5 g of acetic anhydride.

The resulting naphthalene-α-sulphonic acid is fused with 168 g (3 moles) of potassium hydroxide under the conditions described in Example 1 for a period of 30 minutes. Then the melt is dissolved in water and the resulting aqueous solution is acidified with 49 g (0.5 mole) of sulphuric acid. On cooling the acidified solution to a temperature of 10° C., 101 g (0.7 mole) of precipitated α-naphthol with a purity of 99.5% are recovered by filtration.

The filtrate containing potassium sulphite, potassium sulphate and non-precipitated α-naphthol and β-naphthol is treated with an equal volume of cyclohexane, the aqueous layer is separated and cyclohexane is distilled-off to give 36 g (0.25 mole) of α-naphthol with the purity of 98%. The total yield of α-naphthol is 137 g (0.95 mole) which corresponds to 95% of the theoretical value as calculated for the employed naphthalene.

EXAMPLE 3

128 g (1 mole) of naphthalene are mixed with 51 g (0.5 mole) of acetic anhydride and, under stirring, the mixture has added 98 g (1 mole) of a 100% sulphuric acid for a period of 60 minutes to maintain the temperature of the reaction mixture at 85° C. The stirring is continued under vacuum at a residual pressure of 1–2 mm Hg and at a temperature of 85° C., the mixture of 60 g of acetic acid and 9 g of the reaction water is removed. 208 g (1 mole) of the resulting naphthalene-α-sulphonic acid are fused with 124 g (3.1 moles) of sodium hydroxide under the conditions described in Example 1 hereinbefore, but for 30 minutes. The resulting melt is mixed with water in the weight ratio of 1:1 respectively. Then the resulting mixture containing sodium α-naphtholate and sodium sulphite is acidified with an equivalent, relative to sodium α-naphtholate, amount of phosphoric acid and the resulting mixture is cooled to a temperature of 0° C. From the acidified and cooled solution α-naphthol is recovered by filtration to give α-naphthol with a purity of 98.8% in an amount of 138 g which corresponds to 96% of the theoretical value as calculated for the naphthalene employed for the reaction.

EXAMPLE 14

A homogeneous mixture of 128 g (1 mole) of naphthalane, 102 g (1 mole) of acetic anhydride and 98 g (1 mole) of a 100% sulphuric acid is continuously fed into a flow-type tubular reactor at a rate ensuring the residence time of the mixture in a reactor is 120 minutes at the temperature at the reactor inlet of 60° C. and at the reactor outlet temperature of 75° C. The resulting reaction mixture consisting of naphthalene-α-sulphonic acid and acetic acid is continuously fed from the reactor to an evaporator, wherefrom vapors of acetic acid are withdrawn from the top to a cooler and then to a receiver.

From the bottom portion of the evaporator naphthalene-α-sulphonic acid is fed into a flow-type reactor provided with a stirrer and intended for alkali fusion, whereinto simultaneously added are 173.6 g (3.1 moles) of melted potassium hydroxide. The reaction mixture temperature at the fusion reactor inlet is 220° C., at the outlet 285° C.; the time of residence of the reaction mixture in the reactor is 10 minutes. The fusion product (melt) from the reactor is continuously fed into a water-cooled mixer for dilution with 600 g of ethanol (the weight ratio between the melt and ethanol is equal to 1:3). From said mixer the mixture cooled to the temperature of 20° C. is delivered as a suspension to a filter, wherein a filtrate is separated which comprises a solution of potassium α-naphtholate in ethanol. The resulting solution is acidified with the equivalent amount, relative to potassium α-naphtholate, of carbonic acid at a temperature ranging from 60° to 80° C. Then the resulting mixture containing alcohol-dissolved α-naphthol, β-naphthol and potassium carbonate undissolved in ethanol is cooled to a temperature of 20° C. The precipitated potassium carbonate is separated from the solution of α-naphthol and β-naphthol. The alcoholic solution of the naphthols freed from potassium carbonate is delivered to the distillation column to remove ethanol by distillation. From the bottom of said distillation column commercial α-naphthol is fed to close fractionation under vacuum (at a residual pressure of 20–40 mm Hg) and a reflux ratio of 4–6:1. In the first fractionation column there are obtained 116 g of α-naphthol with a purity of 99.5%. The residue from the bottom of the first fractionation column is fed to the second fractionation column, wherefrom 23 g of α-naphthol with a purity of 97% are withdrawn from the top. The residue in the amount of 6 g is recycled to mixing with the residue from the first fractionation column. The total yield of α-naphthol is 139 g (96.5%) of the theoretical value) as calculated for the employed naphthalene.

EXAMPLE 5

An alcoholic solution of potassium α-naphtholate produced as in Example 4 hereinabove is acidified with gaseous hydrochloric acid taken in the equimolar amount relative to potassium α-naphtholate at a temperature ranging from 20° to 30° C. After separation of precipitated pure potassium chloride, the solution of α-naphthol in ethanol is separated following the procedure described in the foregoing Example 4 to give 116 g of α-naphthol with a purity of 97.5%. The total yield of α-naphthol is 140 g (98% of theory) as calculated for the employed naphthalene.

EXAMPLE 6

340 g of a melt, i.e. the fusion product of naphthalene-α-sulphonic acid with potassium hydroxide produced as in Example 4 hereinbefore are diluted with ethylene glycol (the weight ratio between the melt and ethylene glycol is equal to 1:2 respectively). The precipitated potassium sulphite is separated from the solution of potassium α-naphtholate in ethylene glycol by centrifugation. Then the solution of potassium α-naphtholate is acidified with gaseous hydrochloric acid taken in an equimolar amount relative to potassium α-naphtholate. The interaction results in the formation of potassium chloride which precipitates, while the resulting α-naphthol with an impurity of β-naphthol is dissolved in ethylene glycol. After separation of potassium chloride by filtration and vacuum-distillation of ethylene glycol at a residual pressure of 70–80 mm Hg, there are obtained 140 g of a mixture of naphthols consisting of 98.7% of α-naphthol and 1.3% of β-naphthol. From this mixture 114 g of α-naphthol are recovered by close fractionation under a residual pressure of 5–10 mm Hg; a resulting product has the purity of 99.5%.

The residue after fractionation is subjected to vacuum distillation under a residual pressure of 20 mm Hg to give 26 g of α-naphthol.

The total yield of α-naphthol is 140 g which corresponds to 98% of the theoretical value as calculated for the naphthalene employed for the reaction.

What is claimed is:

1. A method for preparing α-naphthol comprising sulphonation of naphthalene with an equimolar amount of concentrated sulphuric acid at a temperature within the range of from 30° to 85° C. for a period of from 60 to 120 minutes in the presence of acetic anhydride taken in an amount of from 0.5 to 1.5 mole per one mole of naphthalene, fusion of the resulting naphthalene-α-sulphonic acid with an alkali taken in an amount of 3–4 moles per mole of the naphthalene-α-sulphonic acid at a temperature of from 180° to 285° C. for 10 to 30 minutes, mixing the resulting melt consisting of an alkali metal α-naphtholate and an alkali metal sulphite with a polar solvent, acidification of the resulting mixture with a mineral acid taken in an equivalent amount relative to the amount of said alkali metal α-naphtholate, followed by isolation of α-naphthol from the resulting suspension.

2. A method as claimed in claim 1, wherein carbonic acid is used for said acidification.

3. A method as claimed in claim 1, wherein the content of naphthalene-β-sulphonic acid in the reaction mixture does not exceed 1% by weight.

4. A method as claimed in claim 1, wherein the polar solvent is selected from the group consisting of water and alcohol.

5. A method as claimed in claim 4, wherein the polar solvent is water and the weight ratio between the melt and water is 1:1–3, respectively.

6. A method as claimed in claim 4, wherein the polar solvent is ethanol.

7. A method as claimed in claim 1, wherein the yield of crystalline α-naphthol of 99.5% purity is 0.7 to 0.8 mole per mole of naphthalene.

8. A method as claimed in claim 1, wherein the content of β-naphthol in the resulting α-naphthol does not exceed 0.5% by weight.

* * * * *